United States Patent [19]
Murphy et al.

[11] Patent Number: 5,256,699
[45] Date of Patent: Oct. 26, 1993

[54] DISPERSIBLE TABLET FORMULATION OF DICLOFENAC ACID FREE BASE

[75] Inventors: Lorraine M. Murphy; Graham P. Matthews, both of Horsham, England

[73] Assignee: Ciba-Geify Corporation, Ardsley, N.Y.

[21] Appl. No.: 869,087

[22] Filed: Apr. 12, 1992

Related U.S. Application Data

[63] Continuation of Ser. No. 691,156, Apr. 24, 1991, abandoned, which is a continuation of Ser. No. 421,578, Oct. 16, 1989, abandoned.

[30] Foreign Application Priority Data

Oct. 18, 1988 [GB] United Kingdom ............. 8824392

[51] Int. Cl.$^5$ ............. A61K 31/135; A61K 9/20
[52] U.S. Cl. ............. 514/658; 514/960; 514/961; 424/464; 424/465
[58] Field of Search ............. 514/557, 658, 534, 535, 514/960, 961; 424/464, 465

[56] References Cited

U.S. PATENT DOCUMENTS

| | | | |
|---|---|---|---|
| 3,558,690 | 1/1971 | Sallmann et al. | 560/47 |
| 4,209,513 | 6/1980 | Towde et al. | 424/228 |
| 4,234,601 | 11/1980 | Gardocki | 424/319 |
| 4,567,178 | 1/1986 | Eberlein et al. | 514/215 |
| 4,609,675 | 9/1986 | Franz | 514/568 |
| 4,711,777 | 12/1987 | Tan | 424/79 |
| 4,774,083 | 9/1988 | Tan et al. | 424/79 |
| 4,867,985 | 9/1989 | Heafield et al. | 424/461 |

FOREIGN PATENT DOCUMENTS 0255002 2/1988 European Pat. Off. .
0324981 7/1989 European Pat. Off. .

OTHER PUBLICATIONS

Pharmaceutical Technology vol. 15, No. 3, pp. 49–56 (1991).

*Primary Examiner*—Frederick E. Waddell
*Assistant Examiner*—T. J. Criares
*Attorney, Agent, or Firm*—Irving M. Fishman; Karen G. Kaiser

[57] ABSTRACT

The invention provides a dispersible solid drug formulation comprising finely divided diclofenac as the free acid, from 5 to 25% by weight of a disintegrant and a pharmaceutically acceptable diluent.

8 Claims, No Drawings

DISPERSIBLE TABLET FORMULATION OF DICLOFENAC ACID FREE BASE

This application is a continuation of application Ser. No. 691,156, filed Apr. 24, 1991, now abandoned, which is a continuation, of application Ser. No. 421,578, filed Oct. 16, 1989, now abandoned.

The present invention relates to a dispersable solid dry formulation containing diclofenac.

Diclofenac is an effective analgesic and antiarthritic agent. It is available, inter alia, as enteric coated tablets and sustained release tablets containing diclofenac sodium, and also as sugar coated tablets of diclofenac potassium.

Some patients are unable or unwilling to swallow tablets, and for these patients, and others, a tablet which disperses in water or other suitable liquid is advantageous because it is more acceptable. Being swallowed in dispersed or dissolved form, the drug is rapidly effective.

If diclofenac sodium is incorporated in a dispersible tablet it dissolves when the tablet is dispersed in water or other suitable liquid producing a liquid with an undesirable bitter taste. Diclofenac potassium also produces a liquid with a bitter taste.

We have found that this difficulty is overcome if diclofenac is dispersed as the free acid rather than as a salt. This has a low solubility and is virtually tasteless.

Accordingly the present invention provides a dispersible solid drug formulation comprising finely divided diclofenac as the free acid, from 5 to 25% by weight of a disintegrant and a pharmaceutically acceptable diluent.

The diclofenac may be in the form of a finely divided powder having a particle size diameter of about 4 to 100 μm.

As disintegrant there may be used compounds such as micro. crystalline cellulose, starches and starch derivatives. Preferably a compound known as a superdisintegrant is used, such as croscarmellose, crospovidone and sodium starch glycollate. In some instances it is advantages to use a combination of disintegrants.

The amount of disintegrant, or mixture thereof, is from 5 to 25%, preferably from 5 to 15%. We prefer to use higher concentrations of disintegrant than is normally used in a conventional (i.e. non-dispersible) formulation.

The formulations of the invention also contain at least one diluent in order to give sufficient material to tablet and facilitate the compression process used to make tablets. Suitable diluents include microcrystalline cellulose, calcium hydrogen phosphate, and lactose. The function of the diluent may be performed by other components, especially. disintegrants.

The formulation of the invention may also contain wetting agents to improve the disintegration and/or dispersion. Suitable wetting agents include dioctyl sodiumsulpho. succinate, polysorbates or sodium lauryl sulphate. The amount of wetting agent is usually not more than 0.1% by weight of the formulation.

The formulation of the invention may also include lubricants, including agents to improve flow. Suitable compounds include fatty acids such as stearic acid, metal stearates such as magnesium stearate, hydrogenated castor oil, talc, and colloidal silicon dioxide. Lubricants may be used in amounts of up to 2% by weight of the formulation.

Colours, flavours and aromatising agents may also be included in the formulations.

The solid drug formulations may be in the form of a simple mixture of the ingredients which can be filled into sachets that can be emptied into water. Preferably the solid drug formulations are in the form of tablets.

Tablets can be manufactured in several known different ways. In the so-called direct compression process a suitable diluent, for example microcrystalline cellulose, selected grades of calcium hydrogen phosphate, or lactose, is chosen to allow the components to be mixed and tabletted.

In the so-called wet granulation process, most of the components of the formulation, including the diclofenac, diluent and all or part of the disintegrant are formed into granules by the addition of a liquid, usually water, and optionally a binding agent. The remaining components such as the remainder of the disintegrant and lubricants are then added and the blend tabletted. If colour and/or flavours are used they may be added at any stage of the process.

The invention is illustrated by the following Examples.

EXAMPLE 1

Diclofenac free acid, lactose and an aliquot of sodium croscarmellose are granulated with an aqueous solution of hydroxypropyl methylcellulose 3 cps and sodium lauryl sulphate in a fluid bed granulator. The granules are dried and then blended with the remaining excipients and compressed into tablets having the following composition.

| | Quantity mg/tablet |
|---|---|
| DICLOFENAC | 46.5 |
| Microcrystalline Cellulose | 100.0 |
| Lactose BP | 100.0 |
| Sodium Croscarmellose | 21.0 |
| Hydroxypropylmethylcellulose 3 cps | 1.82 |
| Hydrogenated Castor Oil | 1.5 |
| Purified Talc | 1.5 |
| Sodium Lauryl Sulphate | 0.045 |
| Total weight of Tablet | 272.365 mg |

EXAMPLE 2

Tablets are made by the method of Example 1 except that calcium hydrogen phosphate is used in place of the microcrystalline cellulose and lactose. The tablets have the following composition.

| | Quantity mg/tablet |
|---|---|
| DICLOFENAC | 46.5 |
| Calcium Hydrogen Phosphate | 200.0 |
| Sodium Croscarmellose | 18.0 |
| Hydroxypropylmethylcellulose 3 cps | 1.82 |
| Hydrogenated Castor Oil | 1.5 |
| Purified Talc | 1.5 |
| Sodium Lauryl Sulphate | 0.045 |
| Total weight of Tablet | 269.365 mg |

EXAMPLE 3

Diclofenac free acid is dry blended with microcrystalline cellulose, sodium crosscarmellose and colouring material. The mass is then wet granulated with water.

The granules are then blended with the remainder of the excipients and compressed into tablets having the following composition.

|  | Quantity mg/tablet |
| --- | --- |
| DICLOFENAC | 46.5 |
| Microcrystalline cellulose | 158.5 |
| F.D.& C. Red No. 3 | 0.3 |
| F.D.& C. Red No. 3/Al Lake | 1.3 |
| Blackcurrant Flavour | 30.0 |
| Sodium saccharin BP | 2.5 |
| Sodium croscarmellose | 14.5 |
| Sodium starch glycollate | 29.0 |
| Hydrogenated Castor Oil | 1.5 |
| Purified Talc | 1.5 |
| Colloidal silicon dioxide | 4.4 |
| Total weight of Tablet | 290 mg |

EXAMPLE 4

Diclofenac free acid is blended with all the excipients other than the lubricant. The mixture is then blended with the lubricant and compressed into tablets having the following composition.

|  | Quantity mg/tablet |
| --- | --- |
| DICLOFENAC | 46.5 |
| Microcrystalline cellulose | 180.2 |
| F.D.& C. Red No. 3 | 0.3 |
| F.D.& C. Red No. 3/Al Lake | 1.3 |
| Blackcurrant Flavour | 30.0 |
| Sodium saccharin | 2.5 |
| Purified Talc | 3.0 |
| Hydrogenated Castor Oil | 3.0 |
| Sodium croscarmellose | 23.2 |
| Total weight of Tablet | 290.0 mg |

EXAMPLE 5

Example 4 is repeated to produce tablets having the following composition.

|  | Quantity mg/tablet |
| --- | --- |
| DICLOFENAC | 46.5 |
| Microcrystalline cellulose | 180.2 |
| F.D.& C. Red No. 3 | 0.3 |
| F.D.& C. Red No. 3/Al Lake | 1.3 |
| Blackcurrant Flavour | 30.0 |
| Sodium saccharin | 2.5 |
| Sodium croscarmellose | 23.2 |
| Magnesium Stearate | 6.0 |
| Total weight of Tablet | 290.0 mg |

We claim:

1. A dispersible solid drug formulation in the form of a tablet comprising finely divided diclofenac in the free acid form having a particle size diameter of from about 4 to about 100 μm, from 5 to 25% by weight of a superdisintegrant selected from the group consisting of croscarmellose, crospovidone, and sodium starch glycollate and a pharmaceutically acceptable diluent.

2. A formulation as claimed in claim 1 in which the amount of superdisintegrant is from 5 to 15% by weight.

3. A formulation as claimed in claim 1 in which the diluent is selected from the group of microcrystalline cellulose, calcium hydrogen phosphate, lactose, and mixtures thereof.

4. A process for the preparation of a dispersible solid drug formulation in form of a tablet as defined in claim 1, which comprises formulating by mixing finely divided diclofenac, in an amount as given in claim 1 or 4, a superdisintegrant selected from the group consisting of croscarmellose, crospovidone, and sodium starch glycollate, and a pharmaceutically acceptable diluent and compressing to tablets.

5. A formulation according to claim 1 further comprising a wetting agent.

6. A formulation according to claim 5 wherein said wetting agent is present in an amount of up to 0.1% by weight of the formulation.

7. A formulation according to claim 1 further comprising a lubricant.

8. A formulation according to claim 7 wherein said lubricant is present in an amount of up to 2% by weight of the formulation.

* * * * *

UNITED STATES PATENT AND TRADEMARK OFFICE
CERTIFICATE OF CORRECTION

PATENT NO. : 5,256,699

DATED : October 26th, 1993

INVENTOR(S) : Murphy et al

It is certified that error appears in the above-identified patent and that said Letters Patent is hereby corrected as shown below:

On the title page, [73] Assignee  , delete "Geify" and insert --Geigy--

Signed and Sealed this

Nineteenth Day of April, 1994

Attest:

BRUCE LEHMAN

Attesting Officer

Commissioner of Patents and Trademarks